United States Patent
Makkonen (10) Patent No.: US 7,390,379 B2
(45) Date of Patent: Jun. 24, 2008

(54) METHOD AND APPARATUS FOR DETERMINING THE LATERAL POSITION OF A WEB OR FABRIC EDGE IN A FORMER

(75) Inventor: Sami Makkonen, Jyväskylä (FI)

(73) Assignee: Metso Paper, Inc., Helsinki (FI)

( * ) Notice: Subject to any disclaimer, the term of this patent is extended or adjusted under 35 U.S.C. 154(b) by 494 days.

(21) Appl. No.: 11/051,847

(22) Filed: Feb. 4, 2005

(65) Prior Publication Data
US 2005/0211404 A1    Sep. 29, 2005

(30) Foreign Application Priority Data
Feb. 5, 2004    (FI)    .................................... 20045028

(51) Int. Cl.
*D21F 7/06*    (2006.01)

(52) U.S. Cl. .................. 162/263; 162/198; 162/252; 162/273; 162/257; 73/159; 73/599; 367/99; 367/118

(58) Field of Classification Search ................. 162/198, 162/252, 263, 273, 257; 73/599, 159, 611; 367/99, 902, 118
See application file for complete search history.

(56) References Cited

U.S. PATENT DOCUMENTS

| 4,077,834 A | 3/1978 | Stark |
| 4,901,292 A | 2/1990 | Schrauwen |
| 4,904,954 A | 2/1990 | Otake et al. |
| 4,914,641 A | 4/1990 | Dorr |
| 5,565,627 A | 10/1996 | Dorr |
| 5,834,877 A | 11/1998 | Buisker et al. |

FOREIGN PATENT DOCUMENTS

DE    39 13 601 A1    10/1990

*Primary Examiner*—Mark Halpern
(74) *Attorney, Agent, or Firm*—Stiennon & Stiennon (57) ABSTRACT

The lateral position of a web or fabric edge 11 in a paper machine is determined using an ultrasonic sensor. The ultrasonic sensor has a detector head 42, with an air channel system which opens to the vicinity of the head for forming an air knife which prevents accumulation of dirt on the head. The protective cover 35 has an air guide 43 extending further than the detector head 42, with air flowing thereabove from inside the protective cover 35 through an opening 36. The end component is on top of the protective cover allowing air to flow from the opening between the air guide and the end component to a detent, which turns the direction of the air flow. This provides efficient cleaning without disturbing, however, the operation of the ultrasonic sensor.

3 Claims, 6 Drawing Sheets

METHOD AND APPARATUS FOR DETERMINING THE LATERAL POSITION OF A WEB OR FABRIC EDGE IN A FORMER

CROSS REFERENCES TO RELATED APPLICATIONS

This application claims priority on Finnish Application No. 20045028, Filed Feb. 5, 2004.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The invention relates to a method utilizing ultrasound for determining the lateral position of a web or fabric edge in a paper machine. The invention also relates to a corresponding apparatus.

U.S. Pat. No. 5,834,877 describes an ultrasonic sensor for determining the web edge position which comprises a U-shape housing. The upper branch of the sensor housing accommodates an ultrasonic transmitter and the lower branch an ultrasonic receiver. The ultrasonic sensor is placed near the web such that the web travels through the gap between the branches. Depending on the position of the web edge, the power received by the ultrasonic receiver varies, based on which the ultrasonic sensor controller determines the edge position relative to the sensor housing. The proposed ultrasonic sensor must be positioned very near to the edge, which makes it vulnerable to damage. In addition, the web must remain accurately in place in the vertical direction, which reduces the positioning options of the sensor housing. Due to its construction and position, the sensor housing also soils easily, and its cleaning is difficult. Furthermore, the proposed ultrasonic sensor cannot be located in humid or hot conditions, which are common in a web-producing paper machine.

Due to demanding conditions, optical sensors, which are based on a photoelectric trip device, are today used in paper machines. In practice, the reflection of light directed to the fabric is detected by adjacent receivers, based on which the position of the edge can be determined. This position information is then used for example for guiding and holding the fabric in a desired position in the cross machine direction of a paper machine. The accuracy of optical sensors, however, is often insufficient. In addition, web moisture or fabric impurities affect the performance of optical sensors, which complicates the control of the apparatus and causes errors. In order to achieve sufficient accuracy, it is necessary to use several sensors, which require separate signal processing equipment for determining the position information with sufficient accuracy. This increases the purchase and operating costs of the apparatus. At the same time, using optical sensors at the so-called wet end of a paper machine is impossible. Optical sensors must also be positioned near the web or fabric, which leads to their soiling and even to damaging.

SUMMARY OF THE INVENTION

The object of the invention is to provide a new method for determining the lateral position of a web or fabric edge in a paper machine, the method being simpler, yet more versatile than heretofore, and avoiding the disadvantages of the prior art technique.

Another object of the invention is to provide a new apparatus for determining the lateral position of a web or fabric edge in a paper machine, which apparatus can be positioned in a paper machine more easily and freely than heretofore and has a simpler and more protected design than heretofore.

The method according to the invention uses ultrasound in a new and surprising way. By using a certain type of ultrasonic sensor and by setting it in a new way, the position of the web or fabric edge can be easily and accurately determined. At the same time, the design of the apparatus remains simple and the ultrasonic sensor can be located in a protected position. By utilizing suitable auxiliary means it is also possible to prevent the ultrasonic sensor from soiling and damaging. Simultaneously, uninterrupted operation of the apparatus can be ensured even in very demanding conditions.

The invention is described below in more detail by making reference to the enclosed drawings illustrating some of the embodiments of the invention.

BRIEF DESCRIPTION OF THE DRAWINGS

FIG. 3b is a fragmentary perspective view of the ultrasonic sensor of FIG. 3a.

DESCRIPTION OF THE PREFERRED EMBODIMENTS

Figure 1:
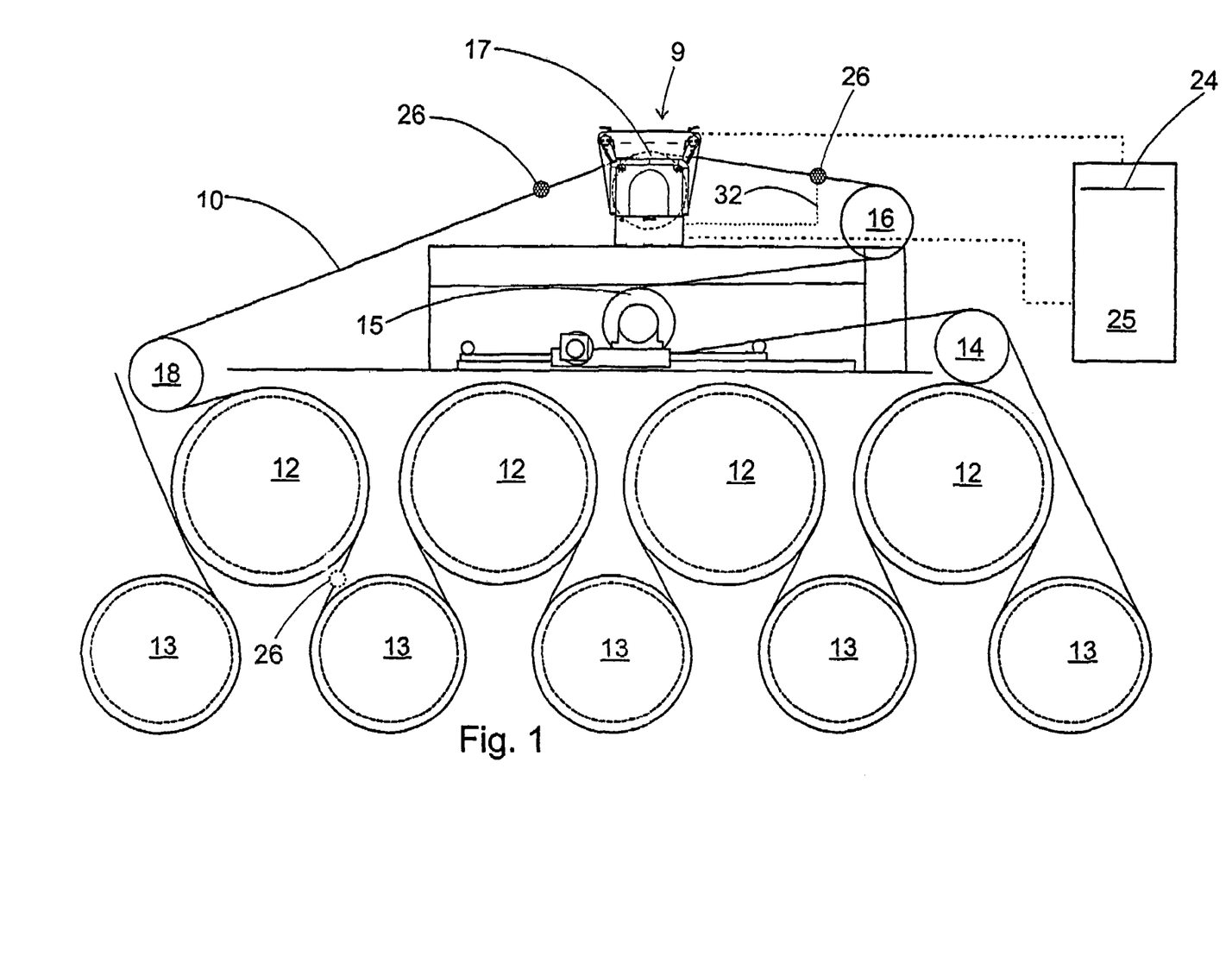
FIG. 1 is a lateral view of a fabric guide arranged in a dryer section of a paper machine.
Figure 2A:
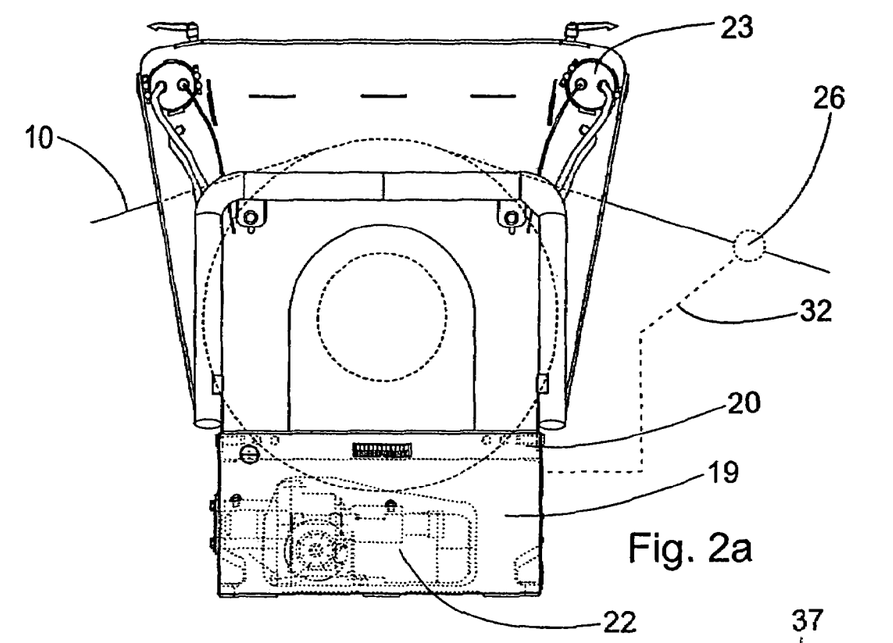
FIG. 2a is a enlarged fragmentary view of the apparatus of FIG. 1.
Figure 2B:
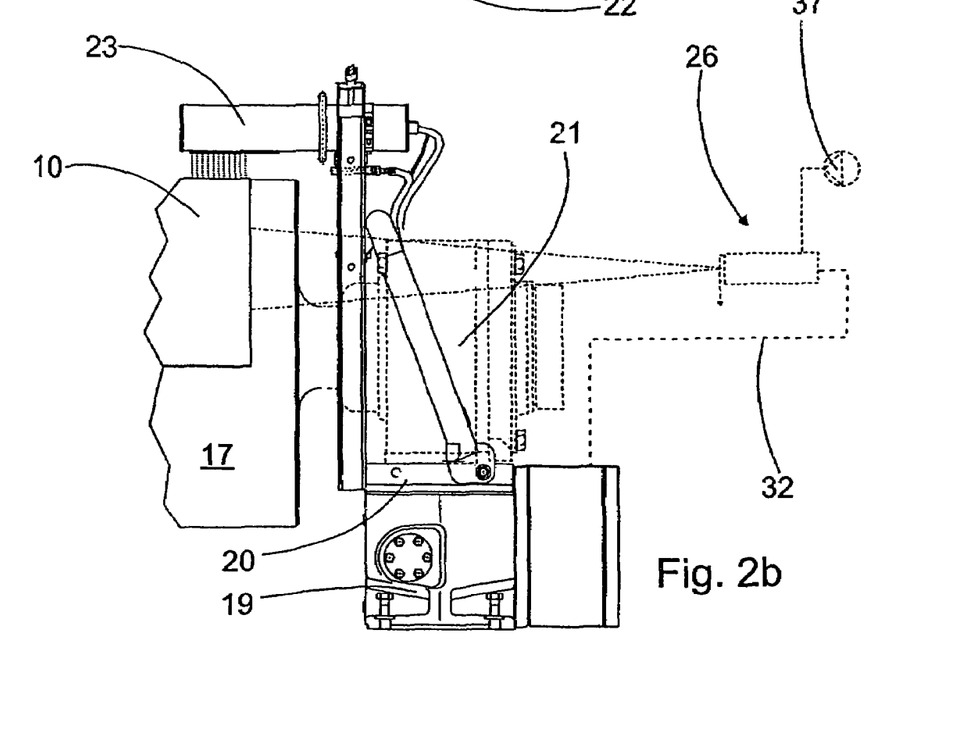
FIG. 2b shows the fabric guide of FIG. 2a seen in the machine direction.

FIG. 1 depicts a known fabric guide 9 arranged in connection with a roll 17 supporting the fabric 10 of a paper machine. The paper machine is used here to refer to a paper or board machine. In the embodiment of FIG. 1 the fabric guide is arranged to guide a dryer fabric serving as the fabric 10, which travels as an endless loop via dryers 12, vacuum cylinders 13 and lead rolls 14-18. In addition to a dryer fabric, the apparatus can be used to guide a press felt, for example, or some other fabric used in a paper machine. Paper machine fabrics are reasonably thin, forming wires are 0.4-2 mm, the press belt and felts are 2-4 mm and the drying wires are 1-2 mm thick, therefore it is very difficult to even the best ultrasonic sensors to measure the distance to the thin edge of the fabric from the side view. In the prior art ultrasonic sensors are used for bigger articles or used as in the aforementioned U.S. Pat. No. 5,834,877. The fabric guide 9 known in the art has two sensor elements 23 as shown in FIGS. 2a and 2b for determining the fabric edge position in the cross machine direction of the paper machine. Each sensor element 23 has a plurality of optical sensors. In order to use the edge position information for fabric guiding, it is additionally required to have a measuring card 24 located in a protected equipment cabinet 25, as shown in FIG. 1. Based on the information collected from the optical sensors it is then possible to determine the position of the fabric edge 11 and thus control the fabric guide. The data transfer channels between the sensor elements, measuring card and fabric guide are represented with dot-and-dash lines in FIG. 1.

FIGS. 2a and 2b show a more detailed illustration of the known fabric guide 9 which is comprised of: a base 19 adapted to be fastened to the paper machine frame, and a transfer base 20 movably adapted to the base 19. Fabric guiding is provided by changing the position of the roll 17. In practice, the bearing pedestal 21 of the roll 17 is fastened to the transfer base 20, which thus moves in the machine direction. The bearing assembly of the roll allows this movement, which can be as long as 100 mm. In practice, however, a movement of a few millimeters is sufficient for providing the desired guiding effect. Installed inside the base 19 there is a suitable motor 22, and the power is usually transmitted to the transfer base 20 by means of a gear system. In addition, the transfer base 20 is movably fastened to the base 19 by means of linear guides (not shown).

The fabric moving on the roll 17 which is rotating at a high speed is continuously moving in the cross machine direction. Therefore its guiding must be continuous. Such guidance is accomplished by moving the end of the roll 17 at all times to keep the fabric at a desired cross machine direction position. For this reason, the known fabric guide as used in the prior art uses the above mentioned sensor elements 23, which are used for determining the axial position of the roll 17 of the fabric 10. In practice, an electronic system connected to the fabric guide continuously compares the measuring results of the optical sensors 23 with the set values and, if necessary, moves the end of the roll 17 over the required distance by controlling the motor 22.

Figure 3A:
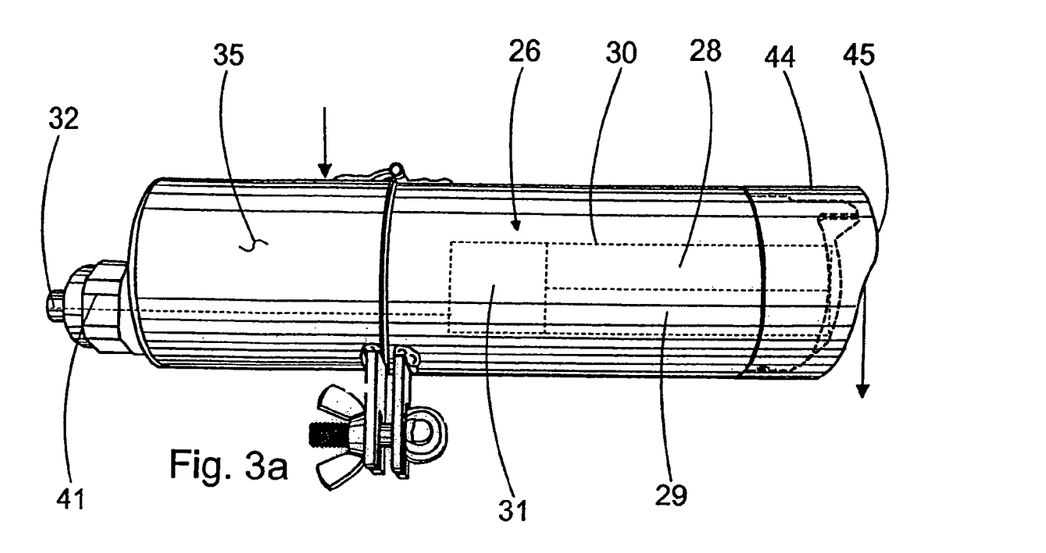
FIG. 3a is a lateral view of an ultrasonic sensor according to the invention.

In place of optical means 23, the method according to the invention uses ultrasound. According to the invention, the edge position of the web 10 is determined by means of a distance measurement. Further the distance measured is made from the sides of the web or fabric 10. This allows positioning ultrasonic measuring equipment 26 far from the web or fabric 10, reducing in this way the soiling of the measuring equipment 26. Furthermore, there is more freedom in the positioning of the equipment 26, and the equipment 26 is smaller and simpler in design than heretofore. More particularly, the distance measured is measured with ultrasound in a cross machine direction away from the web or fabric 10. FIG. 2b shows the measuring equipment 26 according to the invention arranged in connection with the known fabric guide 9. The measuring equipment 26 comprises an ultrasonic sensor having an ultrasonic transmitter 28 and an ultrasonic receiver 29, as shown in FIG. 3a. According to the invention, measuring equipment 26 including the transmitter 28 and receiver 29 can be positioned far from the fabric 10. A suitable measuring distance from the edge 11 of the fabric 10 for the ultrasonic measuring equipment 26 is 400-1000 mm, preferably 501-750 mm. At this distance the measuring equipment 26 can be protected by a frame of a paper machine and still have a straight view to the edge 11 of the fabric. In addition, the measuring equipment 26 can be located more freely than heretofore for measuring web cross machine position at various positions of the fabric run. Two preferable positions of the measuring equipment 26 are shown in FIG. 1 with a shaded circle 26. On the other hand, the ultrasonic sensor can be located in a different position, such as the pocket between the dryers 12 and vacuum cylinder 13 (circle drawn with a broken line). The preferable installation position for the sensor is near the roll 17 that guides the fabric 10, in which case it is possible to achieve feedback control with almost no delay. The guide roll can additionally have integrated fabric stretching or felt squaring or even all these three functions.

Figure 4A:
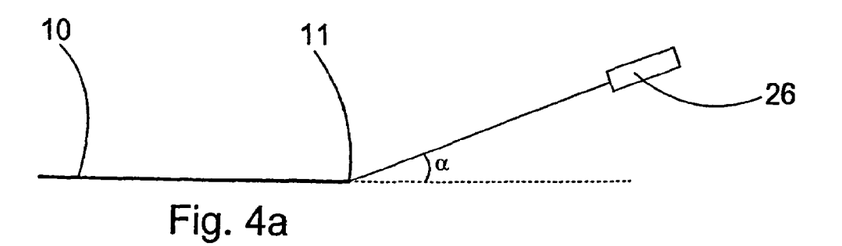
FIG. 4a is a schematic view depicting the locating method relative to the fabric of the ultrasonic sensor according to the invention.
Figure 4B:
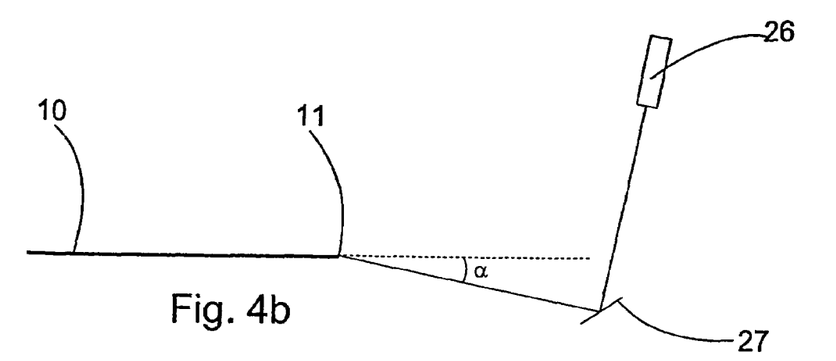
FIG. 4b is a schematic view depicting another locating method relative to the fabric of the ultrasonic sensor according to the invention.

FIGS. 4a and 4b show a schematic drawing indicating the principle of the invention, with the measuring equipment 26 including the ultrasonic sensor 28, 29 (shown in FIG. 3a) located in connection with the fabric 10. Generally the distance measurement is so arranged that between the ultrasonic propagation direction and the plane formed by the web or fabric there is formed an angle a that is smaller than a right angle. The distance is thus measured only at one point. Generally the angle $\alpha$ is 0°-50°, more preferably 0°-10°. With very thin fabrics the best accuracy is achieved with an angle of 1-10 degrees. The effect of reflection from the fabric 10 as opposed to the edge 11 is reduced by diminishing the angle $\alpha$. A measurement made as much as possible from the side is the most accurate in practice. At the same time, the positioning of the ultrasonic sensor in the paper machine is easy. In FIG. 4a the ultrasonic sensor is directed towards the edge 11 of the fabric 10, but the ultrasonic propagation direction can also be changed in the distance measurement by reflecting at least once. This is shown in FIG. 4b, in which there is arranged a suitable reflector 27 between the ultrasonic sensor 26 and the edge 11 of the fabric 10. Here the reflection axis of the reflector is horizontal, but by using a vertical reflection axis the ultrasonic sensor can be positioned, for example, behind the frame beam of the paper machine for protection (not shown). If required, the ultrasonic propagation direction can be changed by reflecting even twice.

According to the invention, the ultrasonic sensor is thus located to the side of the web or fabric. In addition, the ultrasonic sensor is adapted to measure the distance between the ultrasonic sensor and the edge 11 for determining the position of the edge 11. With this solution, determining the edge position is more accurate and easier than heretofore. Also, there is more freedom than before in positioning the ultrasonic sensor. In addition to the fabric edge 11, the measuring equipment 26 can also be used for determining the edge of a paper web or sheet. In summary, the design of the apparatus remains simple, when using the measuring equipment 26, which comprises an ultrasonic transmitter 28 and an ultrasonic receiver 29 adapted in one sensor housing 30 (FIG. 3a). In addition to these, the sensor housing accommodates measuring electronics 31 for processing the information produced by the ultrasonic transmitter 28 and the ultrasonic receiver 29. The measuring electronics can directly provide a voltage or current message, which can be used as such for controlling a fabric guide. The principle of an ultrasonic sensor 26 according to the invention is shown in FIG. 3a with dash lines. The connection cable 32 leading directly from the the measuring equipment 26 to the fabric guide is shown with dash lines in FIGS. 1, 2a and 2b.

When using ultrasound it is important that the sensor is kept in place. Therefore the apparatus comprises support elements 33, shown in FIG. 4c, for locating the ultrasonic sensor preferably at a suitably defined safety distance from the edge 11. The distance can be, for example, 400-1000 mm, preferably 501-750 mm. In practice, a suitable locating distance can be approximately 1000-1500 mm, in which case the ultrasonic sensor can be fastened to the frame constructions of the paper machine or even outside them. According to the invention, the support elements 33 comprise a support arm 34 and a protective cover 35 adapted thereto for the sensor housing. In practice, the support arm is fastened for example to the above mentioned frame constructions (not shown).

Figure 4C:
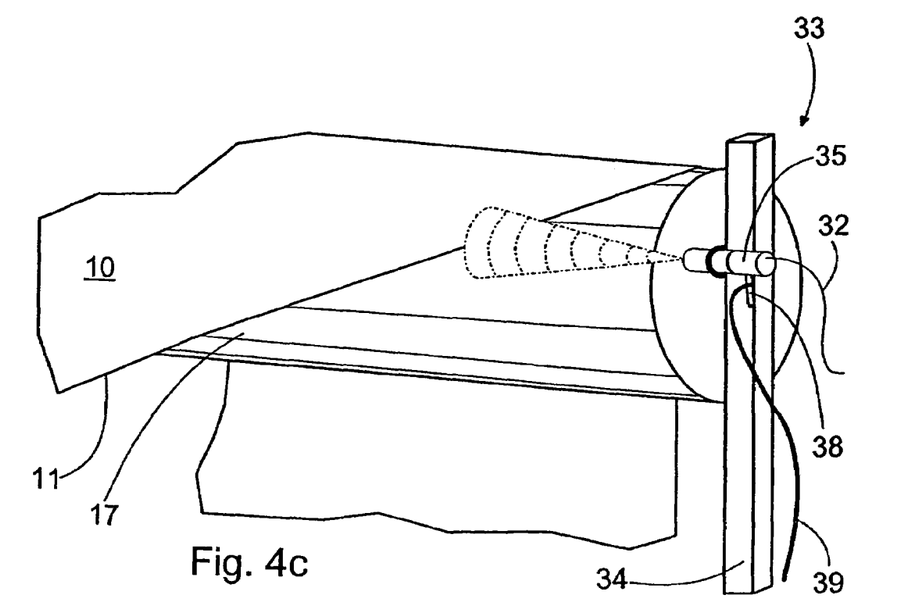
FIG. 4c shows an apparatus according to the invention arranged in connection with a fabric.

The protective cover is essential in particular as regards the performance of the ultrasonic sensor. According to the invention, there is a channel system arranged in the protective cover 35 for cooling the sensor housing 30 and/or keeping the ultrasonic sensor clean by means of an air flow. In other words, air is conducted to the protective cover 35, which, besides providing cooling, keeps the ultrasonic sensor clean. FIG. 2b shows the compressed air source 37. In favorable conditions cooling may be unnecessary, in which case normal compressed air, for example, is used. On the other hand, in hot conditions, a vortex pipe cooler may be connected to the protective cover for providing a cooling air flow inside the protective cover. This is shown in FIG. 4c, in which the vortex pipe 38 with compressed air connections 39 is fastened to the protective cover 35. Tests have shown that the effect of fabric moving and swinging on the measurement, is practically non-existent, and hence the ultrasonic sensor can be located to measure the unsupported part of the fabric. This is particularly true when the ultrasonic sensor is located so the ultrasonic beam is at an angle, which is as small as possible in relation to the fabric.

Figure 3B:
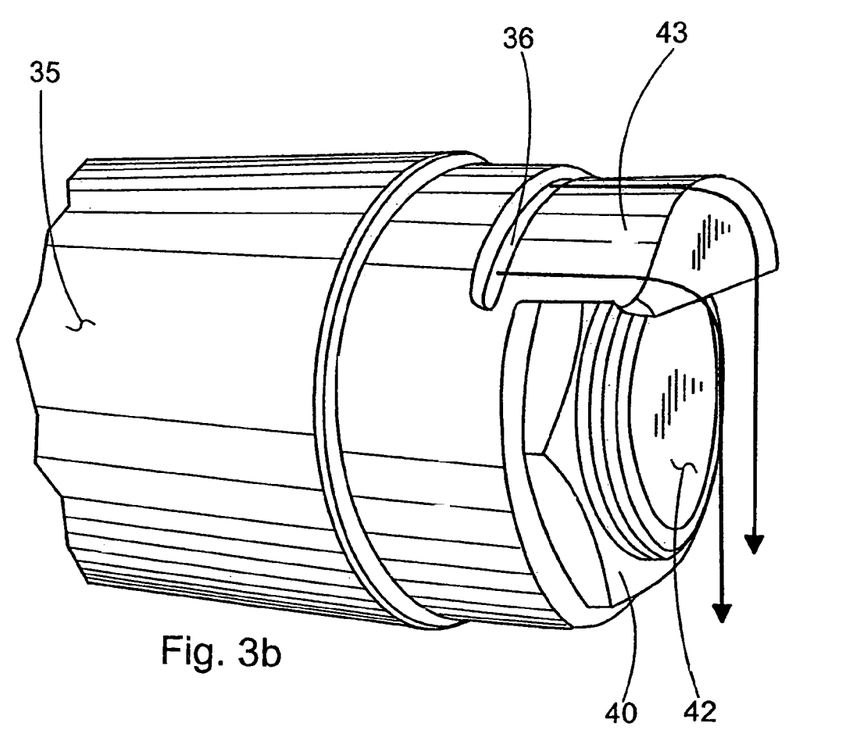

In the exemplifying embodiment the protective cover 35 is a casing made of stainless steel pipe that can be opened at the center. As shown in FIG. 3b, the ultrasonic sensor itself is screwed to the threading arranged at the end wall of the casing. Here the thread is in the nut 40 fastened to the end of the protective cover 35. At the other end of the protective cover 35 there is a lead-through 41 for the connecting cable 32. The ultrasonic sensor is thus fastened to the protective cover only at its end part, allowing cooling air to efficiently surround particularly the electronic components (see FIG. 3a).

Figure 3C:
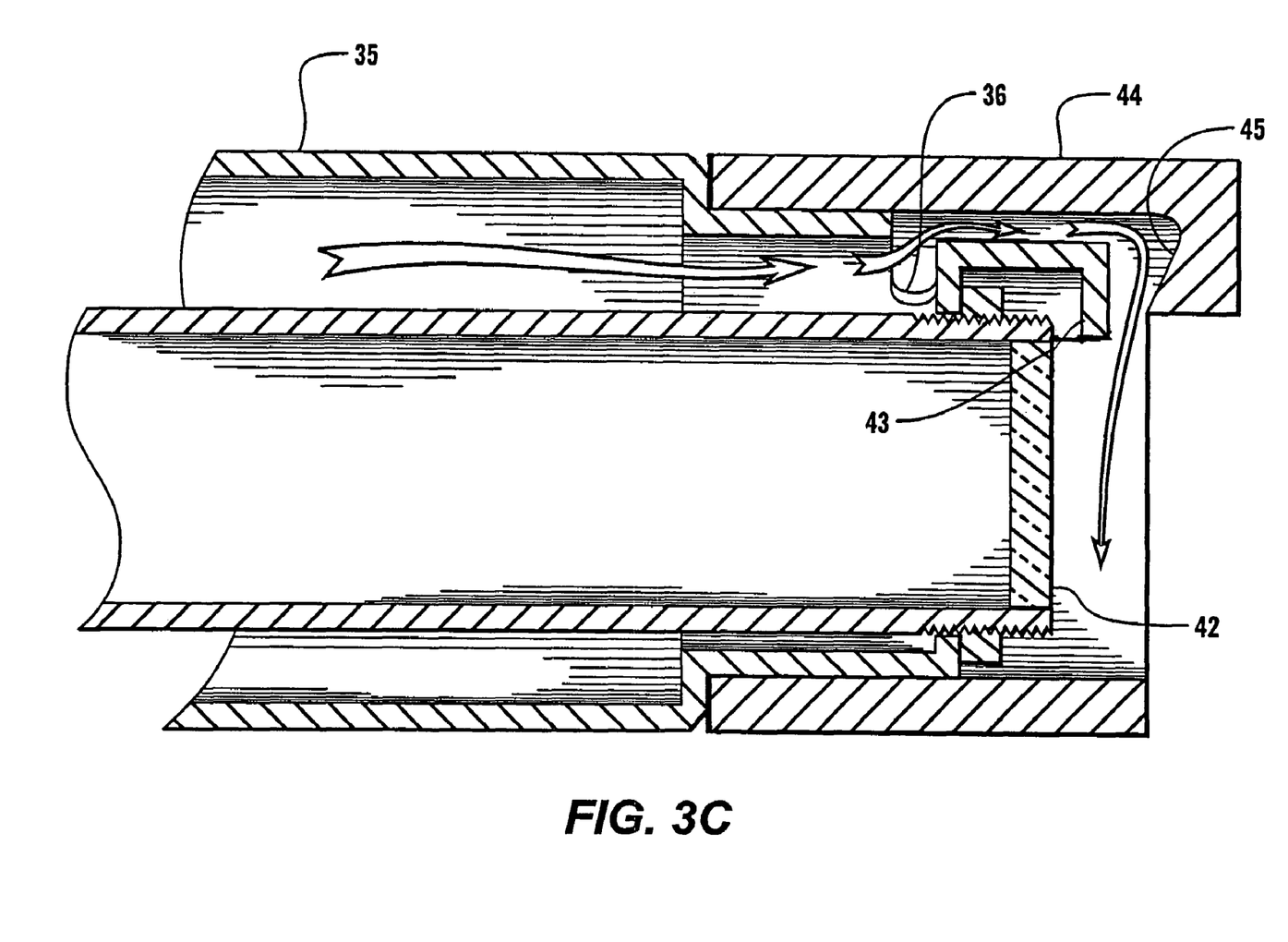
FIG. 3c is a cross-sectional view of the ultrasonic sensor of the invention, showing the air channel system.

The ultrasonic sensor also comprises a detector head 42, which is the only part in connection with the surrounding air. The detector head 42 also has a specific layer, which transmits ultrasonic waves between the detector head and the external air preventing at the same time conduction of heat into the protective cover. According to the invention, the channel system opens to the vicinity of the detector head 42 for forming an air knife. In practice, the air knife prevents accumulation of dirt in the detector head 42. The proposed protective cover 35 has an air guide 43 extending further than the detector head 42, with air flowing thereabove from inside the protective cover 35 through an opening 36. The air guide 43 is shown in FIG. 3b. The protective cover 35 is completed with an end component 44 having a detent 45 designed according to the air guide 43. In the finished protective casing the end component 44 is on top of the protective cover allowing air to flow from the opening between the air guide 43 and the end component 44 to the detent 45, which turns the direction of the air flow, as shown in FIG. 3a. The channel system may be as shown in the embodiment of FIG. 3c. This provides efficient cleaning without disturbing the operation of the ultrasonic sensor. Generally the air knife is arranged essentially in a transverse direction relative to the ultrasonic propagation direction, and the air flow thus preventing temperature variations within the measuring range. Air flows are represented with arrows in FIGS. 3a, 3b, and 3c. The end component 44 and the cover 35 thus have corresponding surfaces which form a fluid channel for the air to flow and cool the open end of the ultrasonic detector. This cooling is desirable because surrounding conditions can be of elevated temperature, for example in the drying section the temperature can be 140° C., which is about twice the temperature usually tolerated by the detector.

Figure 5:
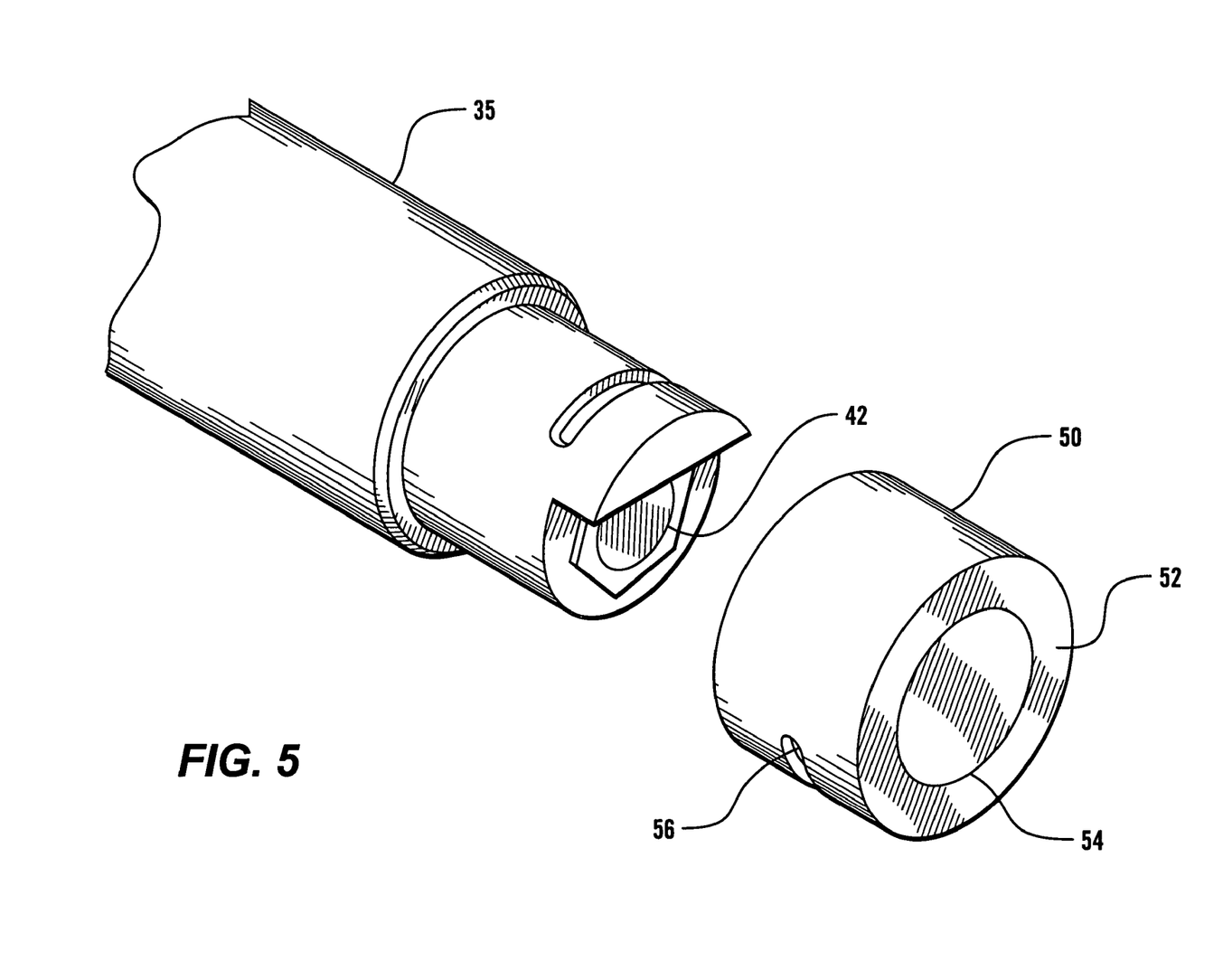
FIG. 5 is a fragmentary exploded isometric view of an alternative embodiment sensor housing of the invention.

Alternatively, as shown in FIG. 5, the cover 35 may have an end component 50 with a dead end wall 52 in front of the detector 42. A portion of the dead end wall 52 is formed by a window 54 formed by a lens or insulant that protects the detector, while not interfering with the propagation of ultrasonic waves therethrough. The end component 50 is then provided with an air outlet opening 56 in its underside for the cooling air to escape. This embodiment may be particularly employed in the wire and press sections, where the added protection against moisture and water is desirable, especially where the water in those regions can include corrosive mater which can cause deterioration in electronics over the long run.

In the ultrasonic sensors used in the apparatus according to the invention, piezoceramic components function as the transmitter 28 and receiver 29. In addition, the detection head 42 has an acoustically thin medium layer through which ultrasound is transmitted to the surrounding air and vice versa. This provides good accuracy for the ultrasonic sensor allowing it to be used even in demanding conditions. The sensor housing 35 itself is watertight. In addition, when using the protective cover 35, compressed air generates an overpressure, which prevents access of moisture to the sensor housing. In practice, the ultrasonic sensor transmits a package of sound pulses and converts the received echo pulses directly into voltage or current messages by means of its measuring electronics. The measuring electronics integrated in the ultrasonic sensor determines the distance based mainly on the echo time and speed of sound. In practice the frequency of ultrasound is approximately 65-400 kHz depending on the sensor type. Correspondingly, the iterative frequency of the sound pulse is approximately 14-140 Hz. The ultrasonic sensor formed a sound cone with a cone angle of 10° in the tested apparatus. The sound cone opens outwardly from the ultrasonic sensor and generally the object is detected if it is in the range of the sound cone or moves across the sound cone. The principle of the sound cone is shown in FIGS. 2b and 4c with dot-and-dash lines. The measuring accuracy of the ultrasonic sensor can be improved, and malfunctions can be minimized by setting with the measuring electronics a certain measuring range, whose echo pulses only are detected by the ultrasonic sensor. In any case, the measuring range of the apparatus according to the invention is multi-tenfold compared to conventional apparatuses.

In addition to analogic current or voltage messages, the ultrasonic sensor can be set as a relay or connected to a computer or other logic system, for example, by means of serial connection. Serial connection also enables changing the settings of the ultrasonic sensor and using versatile measuring functions. The ultrasonic sensor has preferably also a temperature sensor based on which the measuring electronics compensates the effect of the temperature on the operation of the apparatus. In this case, irrespective of changes in conditions, the accuracy and reliability of the apparatus remain unchanged. Ultrasonic precision sensors are particularly suitable for use in the apparatus.

The method according to the invention can be used in various paper machines for monitoring the edge of various webs and fabrics. In addition to fabrics, the method can also be used for example for monitoring and measuring the web and its width as well as for break monitoring. A lateral distance measurement provides an accurate position determination in a simple manner. In addition, the apparatus according to the invention can be freely located in various positions in the paper machine including humid and hot conditions. In practice, the design of the apparatus is simple and the edge position information provided by it can be for example directly used for controlling other apparatuses.

The ultrasonic sensor is particularly good for fast and wide paper machines where the use of mechanical sensors can deteriorate the edges of the fabrics of the paper machine. Wider fabrics for fast machines are also more expensive, so the wear of the fabric edge can be a notable cost when fabric life is shortened. These fabrics can be 5.1 up to 13 meters, preferably 7-13 meters wide. In a fast paper machine, speed over 1000 m/min, more suitable for speeds over 1300 m/min are used. The prior art low cost mechanical sensor solutions are suitable for lower speeds and narrower machines.

It is understood that the invention is not limited to the particular construction and arrangement of parts herein illustrated and described, but embraces such modified forms thereof as come within the scope of the following claims.

I claim:

1. A paper machine apparatus comprising:
    a paper web or fabric run defining a plane, the paper web or fabric run extending in a machine direction over a guide, the guide having a roll which is mounted at one end to a bearing pedestal, the bearing pedestal mounted for movement in the machine direction;
    a motor mounted for driving the bearing pedestal in the machine direction so that the paper web or fabric run can be guided in a cross machine direction, transverse to the machine direction;
    an ultrasonic sensor contained in a housing and fixedly mounted with respect to the paper machine, the housing connected to a supply of compressed air, and arranged to pass cooling air over the ultrasonic sensor, and having portions forming an air knife arranged to blow air to prevent obstruction of the ultrasonic sensor;
    wherein the ultrasonic sensor is arranged to transmit a beam of ultrasonic sound waves towards portions of the paper web or fabric run which define an edge spaced from the roll, so that the beam will reflect from the edge;
    wherein the ultrasonic sensor is arranged to transmit a beam of ultrasonic sound waves which strikes the edge within a plane inclined 0-10 degrees from the plane defined by the paper web or fabric run; and
    wherein the ultrasonic sensor is in controlling communication with the motor so that a measured cross machine position of the edge is used to guide the paper web or fabric run in the cross machine direction.

2. The apparatus of claim 1 wherein the ultrasonic sensor comprises an ultrasonic transmitter and an ultrasonic receiver which are both arranged in the sensor housing.

3. The apparatus of claim 1, wherein the ultrasonic sensor has a detection head, and the air knife directs air over the detection head.

* * * * *